(12) United States Patent
Djurovic

(10) Patent No.: US 9,901,473 B2
(45) Date of Patent: Feb. 27, 2018

(54) ARTIFICIAL SPHINCTER AND INTRAGASTRIC SUSPENDED BALLOON

(71) Applicant: Zarija Djurovic, Chicago, IL (US)

(72) Inventor: Zarija Djurovic, Chicago, IL (US)

(*) Notice: Subject to any disclaimer, the term of this patent is extended or adjusted under 35 U.S.C. 154(b) by 0 days.

(21) Appl. No.: 14/986,659

(22) Filed: Jan. 2, 2016

(65) Prior Publication Data

US 2016/0220405 A1 Aug. 4, 2016

Related U.S. Application Data

(62) Division of application No. 13/624,948, filed on Sep. 23, 2012, now abandoned.

(51) Int. Cl.
*A61F 5/00* (2006.01)
*A61F 2/00* (2006.01)

(52) U.S. Cl.
CPC ............ *A61F 5/003* (2013.01); *A61F 2/0022* (2013.01); *A61F 2/0036* (2013.01); *A61F 5/004* (2013.01); *A61F 5/0036* (2013.01); *A61F 5/0079* (2013.01); *A61F 5/0089* (2013.01); *A61F 2220/0008* (2013.01)

(58) Field of Classification Search
CPC ........................................... A61F 5/00
USPC ............... 623/14.13, 23.64–23.76; 19/14.13, 19/23.64–23.76; 600/30–31, 37; 606/41, 606/191, 192
See application file for complete search history.

(56) References Cited

U.S. PATENT DOCUMENTS

| | | | |
|---|---|---|---|
| 4,118,805 A | 10/1978 | Reimels | 600/30 |
| 2002/0055757 A1* | 5/2002 | Torre | A61B 17/12099 606/192 |
| 2003/0139808 A1 | 7/2003 | Shahinpoor et al. | 623/4.1 |
| 2003/0153905 A1* | 8/2003 | Edwards | A61B 18/1492 606/41 |
| 2005/0283235 A1 | 12/2005 | Kugler et al. | 623/14.13 |
| 2006/0287720 A1 | 12/2006 | Tse | 623/4.1 |
| 2015/0105859 A1 | 4/2015 | Frigstad | A61F 2/0036 623/14.13 |

* cited by examiner

*Primary Examiner* — Yashita Sharma
(74) *Attorney, Agent, or Firm* — Clifford H. Kraft

(57) ABSTRACT

A system of medical devices implantable in the human body using transabdominal gastroscopy surgery to repair failing sphincters and to prevent obesity. An intragastric suspended balloon can be sutured into the stomach to cut appetite. The balloon can be roughly the shape of a pepper and take up room in the stomach without closing it off.

2 Claims, 5 Drawing Sheets

ARTIFICIAL SPHINCTER AND INTRAGASTRIC SUSPENDED BALLOON

This is a divisional of application Ser. No. 13/624,948 filed Sep. 23, 2012. Application Ser. No. 13/624,948 is hereby incorporated by reference in its entirety.

BACKGROUND

Field of the Invention

The present invention relates to medical devices for the human stomach and other passages and more particularly an artificial sphincter and a suspended balloon.

Description of the Problem

A sphincter is a anatomical structure that typically partially or totally closes off a passage in the human body but opens to allow passages of substances. In particular, there is a sphincter where the esophagus enters the stomach, a sphincter where the lower end of the stomach enters the small intestine, a sphincter to the lower end of the colon (anus) and a sphincter below the urinary bladder.

Medical conditions can cause any of these sphincters to partially or totally fail. When the sphincter between the esophagus and stomach fails, highly acid liquid and material can reflux back up into the esophagus causing pain and possible damage to the esophagus. When the pyloric sphincter between the stomach and the small intestine fails, food material enters the small intestine before it is in the proper state of digestion. When the anus fails or partially fails, the patient needs to use bags and other means to control unwanted excretion, and failure or weakness of the urinary sphincter causes incontinence.

It would be advantageous to have an artificial sphincter that could be implanted in the proper location by a general surgeon using transabdominal surgery or gastroscopy assisted by conventional gastroscopy or surgery.

Obesity is a persistent problem in the U.S. and other developed countries. In some cases, it can be controlled by dieting; however, in other cases more invasive medical procedures are needed.

For cases where obesity is caused mainly by overeating, It would be advantageous to have a medical device that could be implanted in the human stomach that would take up space and cause the patient to feel full and stop eating sooner.

SUMMARY OF THE INVENTION

The present invention relates to a system of medical devices that can be implanted in the human body using transabdominal endoscopic surgery to repair failing sphincters and to prevent obesity.

A stainless steel or other medical grade metal or polymer non-magnetic spring covered with silicon or other long-term tissue friendly plastic tubing can be installed in place of a natural sphincter by tunneling through a non-functional natural sphincter and pulling the artificial sphincter into the tunnel to form a ring. The device can be tied on the end with suture to form a permanent structure. Without pressure, the device will be continuously closed; however, it will open under natural pressure on it just as a natural sphincter.

A intragastric suspended balloon can be sutured into the stomach to cut appetite. The balloon can be roughly the shape of a pepper and take up room in the stomach without closing it off.

DESCRIPTION OF THE FIGURES

Attention is now directed to several drawings that illustrate features of the present invention.

Several drawings and illustrations have been presented to aid in understanding the present invention. The scope of the present invention is not limited to what is shown in the figures.

DESCRIPTION OF THE PREFERRED EMBODIMENT

The present invention relates to a system of devices that can be installed using endoscopic surgery. In particular, an artificial sphincter can be installed into any natural sphincter, and an intragastric suspended balloon can be installed in the stomach.

Figure 1:
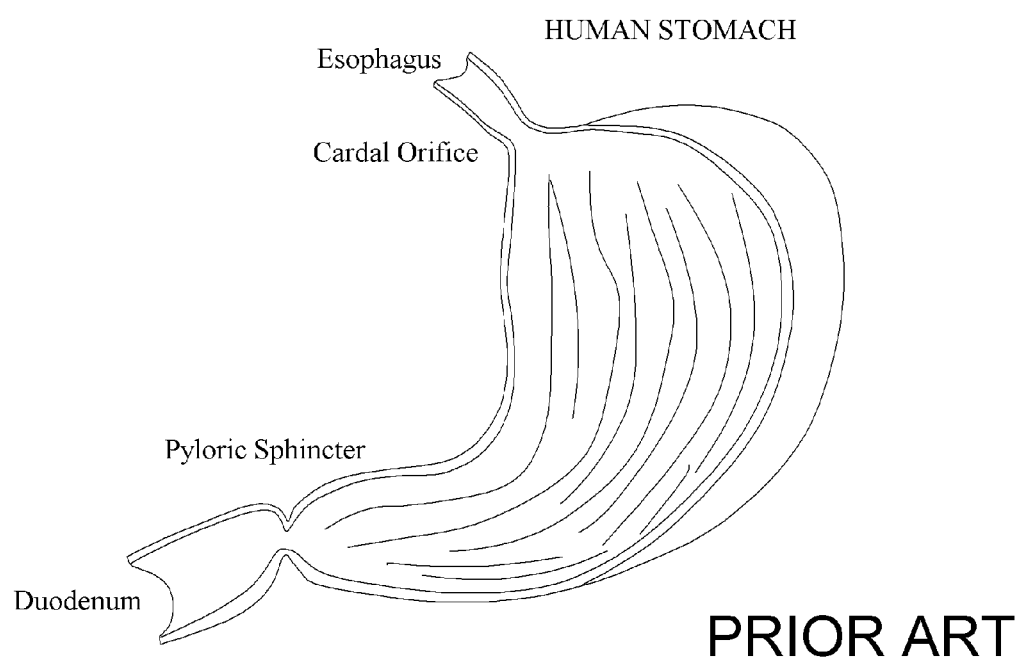
FIG. 1 is a prior art (educational) schematic drawing of a human stomach.

FIG. 1 shows the anatomy of the human stomach. The esophagus feeds through a natural sphincter into the cardal orifice of the stomach. At the lower end of the stomach contents leave the stomach for the small intestine through the pyloric sphincter.

Figure 2A:
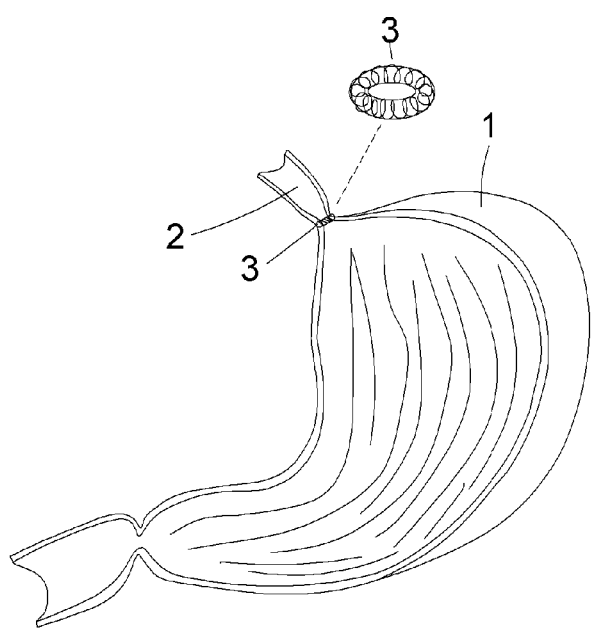
FIG. 2A shows the artificial sphincter of the present invention installed in the esophagus/
Figure 2B:
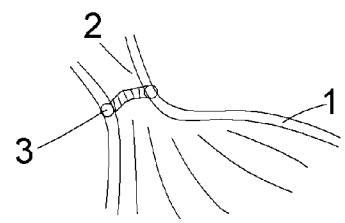
FIG. 2B shows a close-up view of the installation.

FIG. 2A shows installation of the ring-shaped artificial sphincter 3 of the present invention at the bottom of the esophagus 2 in a tunnel made by the surgeon. The wall of the stomach 1 is shown for reference. FIG. 2B shows a close-up of the installation. It can be seen that sits in the tunneled-out natural sphincter and will function by opening and closing directly as pressure from food descending the esophagus. Without pressure, the device will be continuously closed and prevent gastroesphagal reflux of stomach acid into the esophagus.

Figure 3:
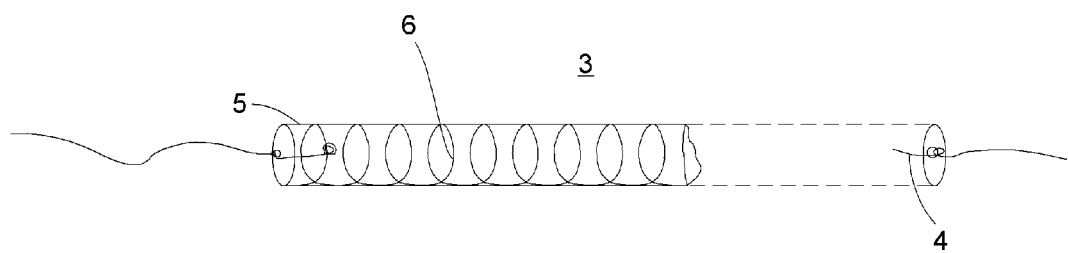
FIG. 3 shows the artificial sphincter laid out flat.

FIG. 3 shows the artificial sphincter 3 laid out flat before installation. A coiled spring 6 runs the length of the device through a tube 5. A string 4 also can attached to each end of the spring 6 and the tube 5 and can be pre-threaded through into device (or the surgeon can thread the device after implantation). The device is covered with silicon tubing 5 or other long term tissue-friendly polymer. The tubing 5 should be fairly tight-fitting and match the diameter of the spring 6.

The spring 6 can be made of non-magnetic stainless steel or other medical grade metal or plastic that will expand from adequate pressure from above or from below. This allows food to enter the stomach from the esophagus during normal eating and for food to exit the stomach during vomiting. The spring 6 is placed in the plastic tubing 5.

After the artificial sphincter is placed into the tunnel made by the surgeon, non-absorbable thread 4 should be tied form a tight ring. Embodiments of the invention can also be supplied with the thread pre-installed.

The implantation procedure can be performed by a general surgeon using transabdominal gastroscopy with the assistance of conventional gastroscopy if needed. The surgeon first performs tunneling through the non-functional natural sphincter and then pulls the artificial sphincter into the tunnel. The device can be threaded (or supplied with threads), pulled into a ring, and tied off.

Figure 4:
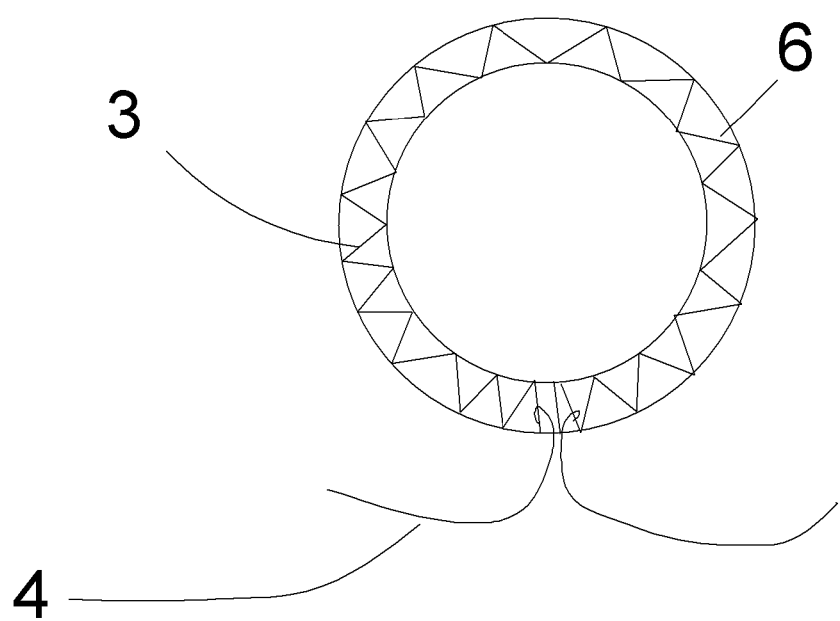
FIG. 4 shows the artificial sphincter in its installed position ready to be tied.

FIG. 4 shows the device of FIG. 3 in a ring configuration.

Figure 5:
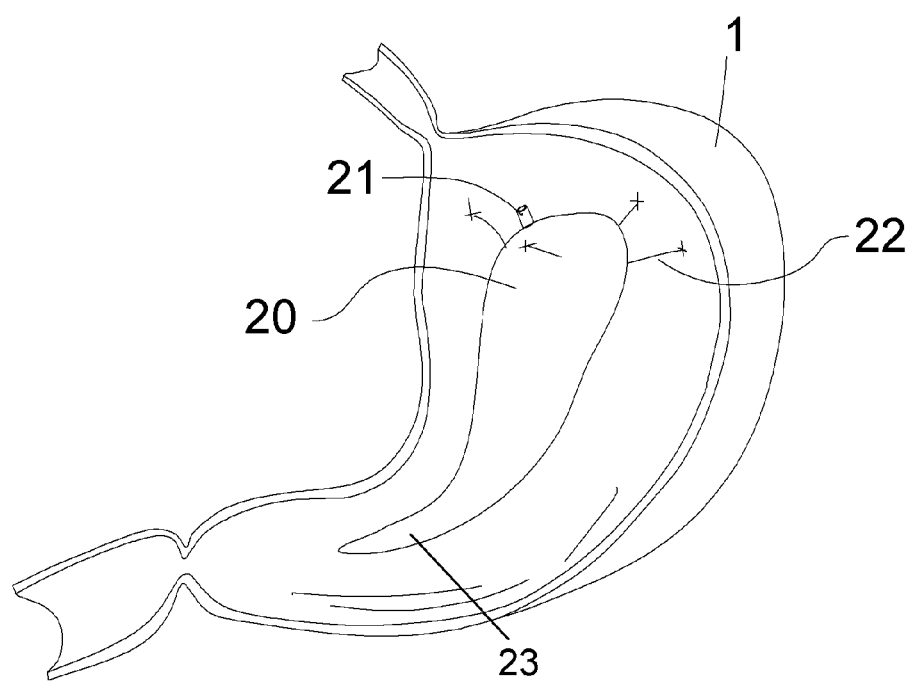
FIG. 5 shows the intragastric suspended balloon in its installed position.

FIG. 5 shows an intragastric suspended balloon for obesity treatment. It is known in the art to place intragastric balloons in the stomach. They have a problem however.

Since they typically float freely, they can sometimes produce symptoms of gastric outlet obstruction. The balloon of the present system is shaped and fixed in place in a particular way. The balloon should occupy about ⅔ of the stomach space more or less, and be constructed in the shape of the stomach with the proximal end 20 round and bigger than the distal end gradually tapering down with the distal end 23 into the atrium. The final size of the installed balloon can be controlled by the amount of fluid-normal saline the surgeon injects to inflate the balloon. The proximal end should have a minimum of four non reabsorbed sutures 22 placed around the larger diameter of the proximal end 20. This suture should be attached to the cardia distally from the gasto-esophageal junction with a free length of 1.5 to 2.0 inches. These ties keep the balloon in an adequate position and will not produce gastric obstructive symptoms. With this embodiment of the invention, the patient feels full much sooner than otherwise.

Installation of the balloon should be performed by a general surgeon with transabdominal gastroscopy with the assistance of conventional gastroscopy if necessary. The balloon has an inflation port 21 that can be inflated through the esophagus or through transabdominal gastroscopy after suturing. The balloon is typically inflated with saline liquid. Any inflating technique that causes the balloon to maintain its shape is within the scope of the present invention.

Evectional removal can be performed by deflating the balloon, cutting the sutures and pulling the balloon out via the esophagus.

Several descriptions and illustrations have been presented to aid in understanding the present invention. One with skill in the art will realize that numerous changes, variations and additions may be made without departing from the spirit of the invention. Each of these changes and variations is within the scope of the present invention.

The invention claimed is:

1. A method of treating obesity comprising:
   supplying an intragastric balloon configured to occupy approximately ⅔ of a patients stomach when inflated, the balloon constructed to conform to the shape of the stomach with a proximal end round and larger than a distal end, said distal end gradually tapering, said balloon having an inflation port on the proximal end;
   situating the balloon in the patients stomach with transabdominal gastroscopy or conventional gastroscopy:
   suturing the proximal end of the balloon to the patient's stomach cardia distally from the gasto-esophageal junction leaving a free length of the balloon of approximately 1.5 to 2.0 inches using at least four non-reabsorbed sutures placed around the diameter of the proximal end of the balloon:
   inflating the balloon with saline solution through the esophagus or through transabdominai gastroscopy using the inflation port after said suturing until the balloon occupies approximately ⅔ of the patient's stomach:
   tying off the inflation port.

2. The method of claim 1 further comprising later removing the balloon evectionally by deflating the balloon, cutting the sutures and pulling the balloon out through the patient's esophagus.

* * * * *